United States Patent [19]

James

[11] Patent Number: 5,269,686
[45] Date of Patent: Dec. 14, 1993

[54] THREADED DRIVABLE DENTAL IMPLANT

[76] Inventor: Robert A. James, School of Dentistry, Loma Linda University, Oral Implantology Center, Loma Linda, Calif. 92340

[21] Appl. No.: 58,262

[22] Filed: May 10, 1993

[51] Int. Cl.⁵ .............................................. A61C 8/00
[52] U.S. Cl. .................................... 433/174; 433/173
[58] Field of Search ....................... 433/173, 174, 175

[56] References Cited

U.S. PATENT DOCUMENTS

| | | | |
|---|---|---|---|
| 2,711,021 | 6/1955 | Parker | 433/174 |
| 4,103,422 | 8/1978 | Weiss et al. | 433/174 |
| 4,268,253 | 5/1981 | Gross et al. | 433/174 |
| 4,746,294 | 5/1988 | Colombo et al. | 433/174 |
| 4,780,081 | 10/1988 | Enomoto et al. | 433/174 |
| 4,863,383 | 9/1989 | Grafelmann | 433/174 |
| 5,087,201 | 2/1992 | Mondani et al. | 433/174 |
| 5,104,318 | 4/1992 | Piche et al. | 433/173 |

Primary Examiner—John J. Wilson
Attorney, Agent, or Firm—James B. Middleton

[57] ABSTRACT

A dental implant has threads with a long pitch so the implant can be driven into a predrilled hole in the bone by axially delivered blows. When rotational forces are placed on the implant in attaching or removing the prosthesis, the long pitch threads will mechanically resist the rotational forces. The implant also includes a post integrally formed thereon so a minimum of separate procedures is required. The post includes a screw having a nylon rod therethrough to lock the screw in place.

12 Claims, 1 Drawing Sheet

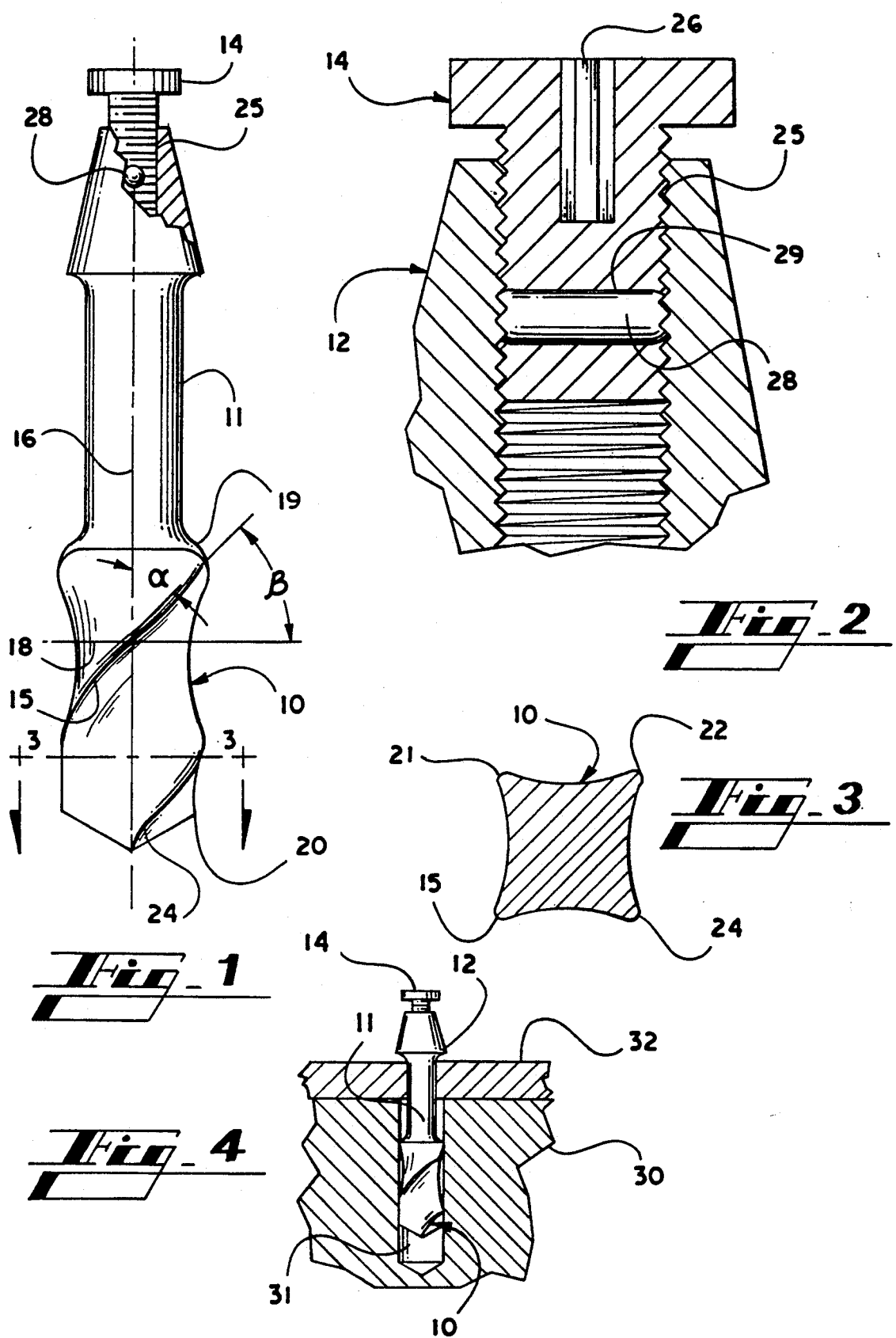

THREADED DRIVABLE DENTAL IMPLANT

BACKGROUND OF THE INVENTION

1. Field of the Invention

This invention relates generally to dental implants, and is more particularly concerned with a drivable implant having torque resisting means.

2. Discussion of the Prior Art

When one or more teeth are to be replaced, it is a common practice to anchor the tooth or teeth prostheses to adjacent teeth. As long as the adjacent teeth are well seated in and secured by bone, the use of adjacent teeth to anchor a prosthesis works quite well. There are, however, times when the adjacent teeth are not sufficiently secure to endure the additional stress encountered in anchoring a prosthesis. In such events, the common practice is to install an implant having a post for securing the prosthesis. The implant is installed by drilling a hole into the bone, and inserting the implant into the bone. A post is then connected to the implant, and the prosthesis is attached to the post, usually by means of a threaded screw. The prosthesis can be installed and removed as desired, and this is done primarily during the fitting stages.

The prior art implants have taken two different forms. In one form, the implant includes a generally straight shank that is driven into the hole in the bone, by tapping with a mallet or the like. This driven implant has the advantage that the implant is quickly placed and is relatively nontraumatic to the bone. The disadvantages of the driven type implant are the fact that only frictional force secures the implant to the bone at the initial installation; and, the driven implant has minimal surface for subsequent tissue attachment. The advantages of the screw-in implant are that the implant is literally screwed into the bone, cutting its own threads in the process, so the screwed-in implant is very secure mechanically on initial installation. Further, the screwed-in implant has a very large surface area because of the threads, and this large surface area promotes attachment of tissue. The primary disadvantage of the screw-in implant is the trauma to the bone caused by the stresses of threading the implant into the drilled hole.

A further difficulty with both the above mentioned types of implants is the likelihood that the implant will be broken loose from its attachment during manipulation of the screw that holds the prosthesis. The driven-in implant has no mechanical means to prevent rotation of the implant, relying only on frictional force and tissue attachment. Both of these can be relatively easily overcome in attempting to remove a screw, especially if the screw has been in place for some time. The screwed-in implant has threads, and will also have some tissue attachment; but, attempting to remove a screw holding a prosthesis can unscrew the screwed-in implant. In either case, it will be understood by those skilled in the art that, once the implant has been broken loose from the tissue attachment, the implant must be removed and replaced.

SUMMARY OF THE INVENTION

The present invention provides a dental implant to be received within a hole drilled in the bone. The lower portion of the implant includes a thread having a long pitch, the crest of the thread forming a small acute angle with a line parallel to the direction of movement of the implant. With the angle of the thread relatively steep, it will be understood that the implant can be driven into the predrilled hole, but will rotate slightly. As the implant is driven into the hole, the crests of the threads will thread themselves into the bone. It is important to note that, if a rotational force is then placed on the implant, the rotational force being about the centerline of the implant, the thread will form a large angle with a line parallel to the direction of motion, so the thread will offer mechanical resistance to rotation of the implant.

In the preferred form of the invention, the threads on the implant comprise a multiple thread to provide balance in the implant. Further, the post is made integrally with the implant, and a screw having a locking means is provided with the implant.

BRIEF DESCRIPTION OF THE DRAWINGS

These and other features and advantages of the present invention will become apparent from consideration of the following specification when taken in conjunction with the accompanying drawings in which:

FIG. 1 is a front elevational view showing an implant and integral post made in accordance with the present invention, a portion thereof being broken away to illustrate the construction;

FIG. 2 is an enlarged, fragmentary view showing the screw for attachment of the prosthesis;

FIG. 3 is a cross-sectional view taken substantially along the line 3—3 in FIG. 1; and, FIG. 4 is a front elevational view of the implant shown in FIG. 1, but on a reduced to scale, and shown implanted for use.

DETAILED DESCRIPTION OF THE EMBODIMENT

Referring now more particularly to the drawings, and to that embodiment of the invention here presented by way of illustration, the device shown in FIG. 1 includes an implant designated at 10 and a neck portion designated at 11. Carried on the neck portion 11 is a post 12, the post 12 having a screw 14 threaded thereinto. It is common in the prior art to provide an implant 10 to be implanted into the bone, and to require that a post, such as the post 12, be subsequently attached to the implant. A prosthesis is then fixed to the post by a screw or the like, such as the screw 14. The present invention therefore simplifies the entire procedure by making the implant 10 integral with the post 12. Of course the screw 14 must remain for use as a fastening means to fix a prosthesis to the post 12.

Looking more specifically at the implant 10, it will be seen that the implant 10 includes threads 15. The threads 15 have a very long pitch, which is to say there is a large distance between adjacent crests of a thread. The important aspect of the long pitch is that the angle a between the crest of the thread 15 and the centerline 16 of the implant 10 is relatively small. When the implant is being driven in, the direction of the force will be along lines that are parallel to the centerline 16.

It will be understood that, if the angle $\alpha$ were zero the threads 15 would amount to longitudinal ridges on the implant, and if the angle $\alpha$ were 90° the threads 15 would be concentric rings around the implants. Thus, by making the angle $\alpha$ greater than zero but very small, a thread is achieved that will allow the implant to be driven into a predrilled hole. Since the crests of the threads 15 will engage the bone as the implant is driven in, the implant will rotate and the implant will cut its own threads into the bone. The specific angle α is somewhat variable, but it is preferred that the angle be around 20° to 25°, though the angle α may be as large as about 30°.

When a rotational force is placed on the implant, the force being about the centerline 16, threads 15 will counteract the force. In this direction, one must consider the angle β which is the angle between the thread 15 and a perpendicular 18 to the centerline 16, which is also parallel to the direction of the force applied on the implant. If the angle β is very small, the rotational force will be almost along the ridge of the thread, but if the angle β is large, the rotational force will be approaching a perpendicular to the crest of the thread. It will be recognized that, if the angle α is 20°, the angle β will be 70°, the angles being complementary.

With the long pitch threads here contemplated, it will be readily understood that, in a conventional length of implant, there would probably be only a single thread. As a result, in order to balance the implant, and render the device more stable, it is contemplated that a multiple thread will be used. In the embodiment here presented by way of illustration, a quadruple thread is utilized as is best shown in FIG. 3 of the drawings. Looking at FIG. 1 in conjunction with FIG. 3, it will be understood that the four separate threads begin at the top 19 of the implant 10, and each of the threads 15 extends helically down to the lower end 20 of the implant 10. There are therefore four crests of threads designated at 15, 21, 22 and 24.

Turning now to the post 12 shown in FIG. 1 of the drawings, and looking also at FIG. 2 of the drawings, it will be seen that the post 12 is a generally frustoconical member here shown as formed integrally with the neck 11. The post 12 defines a threaded opening 25 for selectively receiving the threaded screw 14. As is known in the art, the screw 14 includes a hexagonal socket 26 to receive an Allen wrench for rotation of the screw 14.

Those skilled in the art will realize that, sometimes screws such as the screw 14 will become loose after the prosthesis has been put into place and the screw tightened. The loosening is due to normal cyclic forces on the prosthesis. In an effort to counteract these forces and hold the screw 14 in place, the present invention includes a locking means 28. The locking means 28 comprises a deformable rod received within a hole 29 that extends diametrically through the screw 14. The rod 28 will normally protrude slightly beyond the threads on the screw 14 so that, when the screw 14 is received within the threaded opening 25, the rod 28 will be deformed by the threads. The rod 28 therefore serves to jam the screw 14 into place. The rod 28 may be made of any one of numerous materials, such as nylon or other plastic elastomeric materials, or may be made of natural or synthetic rubber or the like.

With the foregoing description in mind, attention is directed to FIG. 4 of the drawings. FIG. 4 illustrates a device of the present invention as it would be installed. The bone into which the implant is installed is designated at 30, the bone 30 defining a drilled hole 31 therein. It will be seen that the implant 10 is received completely within the hole 31, and the neck 11 extends through the hole 31, then through the gum tissue 32. The post 12 is above the gum 32 for receipt of the prosthesis. The gum 32 is here shown as closely surrounding the neck 11, and it will be understood that this will be the situation after the implant has been installed and the soft tissue has healed.

When a prosthesis is to be installed on the post 12, the screw 14 will be removed, and the prosthesis will be put into place on the post 12. The screw 14 will then be replaced and firmly tightened. When the screw 14 is tightened, it will be understood that a rotational force will be applied on the implant 10. Due to the angle of the thread 15, it will be understood that there will be a great force resisting rotation of the implant 10 so the implant 10 is unlikely to rotate within the hole 31. If the prosthesis must then be removed for further fitting or the like, removal of the screw 14 will require a rotational force on the implant in the opposite direction. In this case, the thread 15 will also present a large counteracting force so that the implant 10 is unlikely to be rotated.

After the implant has been in place for a period of time, tissue will attach to the implant and assist in resisting rotation. After attachment of the tissue, if the implant is caused to rotate, the tissue will be destroyed and the implant must be removed and replaced. In the present invention, the mechanical arrangement is such that there is mechanical force that protects the tissue growth so that the implant is unlikely to fail and have to be removed. Further, due to the additional surface area caused by the presence of the multiple threads, it will be understood that there will be a considerable amount of tissue attachment to the implant of the present invention.

Those skilled in the art will understand that the implants of the present invention can be made in numerous sizes, and with various thread arrangements. By way of illustration without any intent to limit the scope of the present invention, one successful embodiment of the invention has a major diameter on the implant of about 3.5 millimeters and a threaded length of around 7 to 13 millimeters. In this embodiment, the threads have a pitch of one thread per inch (1 thread in 25.4 mm), and there are four threads.

From the top of the thread to the bottom of the post might be around 8 millimeters, and the post itself may be around 4 millimeters high. The implant of the present invention has been made of a conventional titanium alloy as is well known for use in dentistry, but those skilled in the art will readily select other materials that serve as well.

It will therefore be understood by those skilled in the art that the particular embodiment of the invention here presented is by way of illustration only, and is meant to be in no way restrictive; therefore, numerous changes and modifications may be made, and the full use of equivalents resorted to, without departing from the spirit or scope of the invention as outlined in the appended claims.

I claim:

1. A dental implant to be received within a hole drilled into the bone, said dental implant including a lower threaded portion having an axis, and an upper neck portion, said lower threaded portion and said neck portion being coaxial, said lower threaded portion including at least one thread extending throughout said lower threaded portion and including a crest of said thread, said crest of said thread forming an acute angle of no more than 30° with said axis, so that said implant is adapted to be driven into said hole drilled into the bone by forces exerted axially of said implant.

2. A dental implant as claimed in claim 1, wherein said acute angle is from 20° to 25°.

3. A dental implant as claimed in claim 1, said at least one thread comprising a multiple thread, the threads of said multiple thread being uniformly spaced around said implant.

4. A dental implant as claimed in claim 3, said multiple thread comprising four threads.

5. A dental implant as claimed in claim 1, said implant further including a post carried on said neck portion, the dimensions of said implant being such that said threaded portion will be received within said hole drilled into the bone, said neck portion will extend from said hole to above the gum line, and said post will be disposed above said gum line.

6. A dental implant as claimed in claim 5, said post defining a threaded recess therein, a screw threadedly receivable within said recess, and locking means for securing said screw within said recess.

7. A dental implant as claimed in claim 6, said screw defining a bore laterally therethrough, said locking means comprising a deformable rod received within said bore and engageable with the threads in said threaded recess.

8. A dental implant as claimed in claim 7, wherein said rod consists of a thermoplastic elastomer.

9. A dental implant, of the type wherein a hole is drilled into the bone for receiving the implant, and the implant carries a post above the gum line for attachment of a prosthesis, said implant including a threaded portion to be received within said hole and having an axis, and a neck portion extending coaxially from said threaded portion through the soft tissue, said threaded portion having a multiple thread extending throughout the length of said threaded portion, each thread of said multiple thread being disposed at an acute angle of no more than 30° with respect to said axis so that said implant can be driven into said hole by forces exerted axially of said implant, the arrangement being such that said implant will rotate somewhat under the influence of said threads as said implant threads into said hole.

10. A dental implant as claimed in claim 9, and further including a post carried on said neck portion, the dimensions of said implant being such that said threaded portion will be received within said hole drilled into the bone, said neck portion will extend from said hole to above the gum line, and said post wall be disposed above said gum line.

11. A dental implant as claimed in claim 10, said post defining a threaded recess therein, a screw threadedly receivable within said recess, and locking means for securing said screw within said recess.

12. A dental implant, of the type wherein a hole is drilled into the bone for receiving the implant, and the implant carries a post above the gum line for attachment of a prosthesis, said implant including a threaded portion to be received within said hole, and a neck portion extending coaxially from said threaded portion through the soft tissue, said threaded portion having a multiple thread extending throughout the length of said threaded portion, said multiple thread being at such an angle that said implant can be driven into said hole by forces exerted longitudinally on said implant, the arrangement being such that said implant will rotate somewhat under the influence of said threads as said implant threads into said hole, and further including a post carried on said neck portion, the dimensions of said implant being such that said threaded portion will be received within said hole drilled into the bone, said neck portion will extend from said hole to above the gum line, and said post will be disposed above said gum line, said post defining a threaded recess therein, a screw threadedly receivable within said recess, and locking means for securing said screw within said recess, said screw defining a bore laterally therethrough, said locking means comprising a deformable rod received within said bore and engageable with the threads in said threaded recess.

* * * * *